United States Patent
Kwak et al.

(10) Patent No.: US 8,685,496 B2
(45) Date of Patent: Apr. 1, 2014

(54) METHOD OF FABRICATING ALIGNMENT LAYER OF LIQUID CRYSTAL DISPLAY DEVICE AND TESTING THE ALIGNMENT LAYER

(75) Inventors: Musun Kwak, Paju-si (KR); Jae-Ha Choi, Gumi (KR); Hanrok Chung, Daegu (KR)

(73) Assignee: LG Display Co., Ltd., Seoul (KR)

( * ) Notice: Subject to any disclaimer, the term of this patent is extended or adjusted under 35 U.S.C. 154(b) by 722 days.

(21) Appl. No.: 12/346,079

(22) Filed: Dec. 30, 2008

(65) Prior Publication Data

US 2009/0169754 A1    Jul. 2, 2009

(30) Foreign Application Priority Data

Dec. 31, 2007    (KR) .................. 10-2007-0141972

(51) Int. Cl.
    *B05D 3/02* (2006.01)
(52) U.S. Cl.
    USPC .................................................. 427/379
(58) Field of Classification Search
    USPC .................................................. 427/379
    See application file for complete search history.

(56) References Cited

U.S. PATENT DOCUMENTS

| | | | |
|---|---|---|---|
| 5,477,360 A * | 12/1995 | Sunohara et al. | 349/132 |
| 5,969,055 A * | 10/1999 | Nishikawa et al. | 525/419 |
| 2004/0062878 A1 * | 4/2004 | Mano et al. | 428/1.1 |
| 2006/0051525 A1 * | 3/2006 | Tsutsui et al. | 428/1.26 |
| 2007/0125405 A1 * | 6/2007 | Sekiguchi et al. | 134/34 |
| 2007/0153216 A1 * | 7/2007 | Kim | 349/156 |

FOREIGN PATENT DOCUMENTS

| | | |
|---|---|---|
| KR | 100252223 B | 1/2000 |
| KR | 2003-19247 | 3/2003 |
| KR | 2004-110833 | 12/2004 |
| KR | 1020050057043 A | 6/2005 |

OTHER PUBLICATIONS

Kim et al "Nano-rubbing of a Liquid Crystal Alignment Layer by an Atomic Force Microscope: a Detailed Characterization" Nanotechnology 13 (2002) 133-137.*
Screen capture on Oct. 10, 2012 of http://en.wikipedia.org/wiki/isopropyl_alcohol.*
Office Action issued in corresponding Korean Patent Application No. 10-2007-0141972, mailed Dec. 7, 2010.
Office Action issued in corresponding Korean Patent Application No. 10-2007-0141972, mailed Sep. 20, 2011.

* cited by examiner

*Primary Examiner* — Nathan Empie
(74) *Attorney, Agent, or Firm* — Brinks, Gilson & Lione

(57) ABSTRACT

An alignment layer is tested using an AFM (Atomic Force Microscope) and a FT-IR (Fourier Transformation Infrared Spectroscope) under various process conditions so that inferiority of the alignment layer can be detected and optimum process conditions can be obtained, thereby minimizing the inferiority of the alignment layer by applying the optimum process conditions.

5 Claims, 3 Drawing Sheets

S201 — COATING POLYAMIC ACID

S202 — DRYING AT 145 °C~180 °C FOR 80~100 SECOND

S203 — BAKING AT 230 °C OR 240 °C FOR MORE THAN 1000 SECOND

S204 — DIPPING ALIGNMENT LAYER IN 20~30% ISOPROPANE SOLUTION 30~90 SECOND

METHOD OF FABRICATING ALIGNMENT LAYER OF LIQUID CRYSTAL DISPLAY DEVICE AND TESTING THE ALIGNMENT LAYER

RELATED APPLICATIONS

The present invention claims the benefit of Korean Patent Application No. 141972/2007 filed in Korea on Dec. 31, 2007, which is hereby incorporated by reference.

BACKGROUND

1. Field of the Disclosure

This invention relates to a method of fabricating an alignment layer of the liquid crystal display device and testing the alignment layer, and more particularly to the rapid testing method of the alignment layer and fabrication method of the alignment layer progressed in the optimum condition.

2. Description of the Related Art

A liquid crystal display device controls the transmittance of the light through a liquid crystal layer using the anisotropy of the refraction of the liquid crystal molecule to display the image. In this liquid crystal display device, the alignment layer should be rubbed to provide the alignment controlling force to the alignment layer in order to arrange the liquid crystal molecules along the desired direction.

The alignment is mainly made of an polyimide-base material. The polyimide-base polymer is reacted with a diamine compound and an anhydride in a solvent to form a polyamic acid. This polyamic acid solution is deposited on the substrate and then dehydrated through the drying and curing processes to form the polyimide thin film. In general, the polyamic acid element remains in the polyimide alignment layer when the deposited polyamic acid solution, since the polyamic acid solution is not perfectly dried. In order to dry the polyamic acid solution perfectly, the deposited polyamic acid solution should be heated for a long time, but this causes the damage of the alignment. Thus, the polyamic acid solution is heated in the predetermined period and thus the polyamic acid element remains in the polyimide alignment layer. This means that the actual alignment layer includes a polyamic acid layer and a polyimide layer.

The voltage holding ratio of the polyimide layer is high, while the voltage holding ratio of the polyamic acid layer is low. However, the polyamic acid layer has advantages of not having the direct current remain and the good boundary characteristic. Thus, if the alignment layer includes the polyamic acid layer and the polyimide layer, the alignment characteristic of the alignment layer can be improved, and the remaining of the direct current in the alignment layer can be prevented, and the adhesion between the alignment layer and the other layers contacted therewith can be improved.

The test of the alignment layer is conducted after fabricating the liquid crystal display panel. The alignment layer is tested by the MPS (Mass Product System) test which is mainly used for testing the liquid crystal display panel. This MPS test detects the line defect or the point defect of the liquid crystal display panel. In this MPS test, the gate pad and the data pad of the liquid crystal display panel are respectively connected to the gate shorting bar and the data shorting bar and the test signal is applied to the pixel through the gate shorting bar and the data shorting bar to detect the test value so that the inferiority may be judged based on the detected test value.

There are several reasons of inferiority for the liquid crystal display panel, for example, the inferiority of thin film transistor, opening of the metal pattern, and inferiority of the alignment layer. Thus, in order to understand the reason for the inferiority of a liquid crystal display panel, the user should observe the inferiority pattern of the liquid crystal display panel, take a picture of the alignment layer using a CCD camera to analyze the picture after removing the liquid crystal layer from the liquid crystal display panel, or take a picture of the thin film transistor or the metal pattern using the CCD camera to analyze the picture after removing the alignment layer from the liquid crystal display panel.

However, there are some problems with this testing method of the alignment layer.

First, there is no test process for testing solely the alignment layer in the related art. Thus, in the related art, the liquid crystal display panel should be tested as well to test the alignment layer of the liquid crystal display panel. That is, the liquid crystal display panel is completely fabricated and the test signal is inputted to the completed liquid crystal display panel to test the alignment layer. Accordingly, there is a limitation for testing the alignment layer and rapid testing is impossible.

Second, in the related art, since there is no test process for testing solely the alignment layer, various tests for the alignment layer such as testing the dry condition or the cleaning condition of the alignment layer, etc., is impossible.

Third, in the related art, since the various tests for the alignment layer is impossible, it is impossible to obtain the optimum condition for forming the alignment.

BRIEF SUMMARY

A testing method of the alignment layer comprises providing a substrate on which an alignment material is coated, the alignment material including a polyamic acid; drying the alignment material and then observing the dried alignment material by taking a picture using an AFM (Atomic Force Microscope); and baking the alignment material and then detecting the property of the baked alignment material using a FT-IR (Fourier Transformation Infrared Spectroscope).

The fabrication method of the alignment layer comprises coating an alignment material on the substrate; drying the alignment material at the actual temperature of about 60-70° C. for about 80-100 seconds; baking the dried alignment material at the temperature of about 230° C. or about 235° C. for more than about 1000 seconds; and cleaning the baked alignment material The foregoing and other features and aspects of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE DRAWINGS AND THE PRESENTLY PREFERRED EMBODIMENTS

Reference will now be made in detail to the preferred embodiments of the present invention, examples of which are illustrated in the accompanying drawings.

Figure 1:
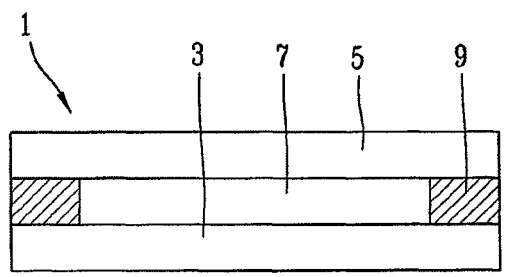
FIG. 1 is a view showing the structure of the liquid crystal display device.

Referring to FIG. 1, the liquid crystal display device includes a first substrate 3, a second substrate 5, and a liquid crystal layer 7 between the first substrate 3 and the second substrate 5. The first substrate is an array substrate. Not shown in FIG. 1, a plurality of pixels are formed in the first substrate 3 and a driving device such as a thin film transistor is formed at each pixel. The second substrate 5 is a color filter substrate having a color filter layer representing color. Further, a pixel electrode is formed on the first substrate and a common electrode is formed on the second substrate. On the first substrate 3 and the second substrate 5, the alignment layer for aligning the liquid crystal molecules are formed.

The first substrate 3 and the second substrate 5 are attached each other by a sealing material 9. A liquid crystal layer is formed between the attached first and second substrates 3 and 5 so that the liquid crystal molecules in the liquid crystal layer are driven to control the amount of the light transmitting the liquid crystal layer in order to display image.

Fabrication processes for LCD devices may be roughly divided into a driving device array fabrication process, where driving devices are formed on the first substrate 3; a color filter fabrication process, where the color filter is formed on the second substrate 5; and a cell fabrication process. These fabrication processes will now be described with reference to FIG. 2.

Figure 2:
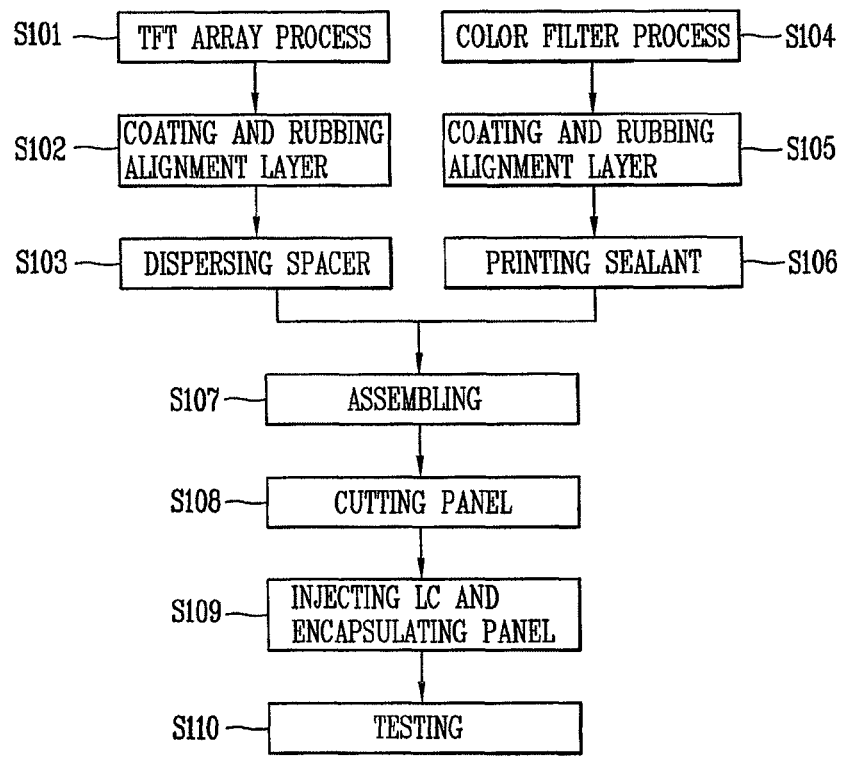
FIG. 2 is a flow chart showing the method of fabricating the liquid crystal display device.

Referring to FIG. 2, in the driving device array substrate fabrication process (S101), a plurality of pixel areas are formed at crossings of a plurality of gate lines and data lines formed on the first substrate 3, and thin film transistors arranged in each pixel area are connected to gate lines and the corresponding data lines. Also, pixel electrodes are connected to each of the thin film transistors to drive the liquid crystal material layer. Accordingly, the liquid crystal material layer may be driven in accordance with a signal applied to the thin film transistor.

In the color filter fabrication process (S104), red (R), green (G), and blue (B) color filter layers for producing color and a common electrode are formed on the second substrate 5.

The alignment layer is formed on both the first and second substrates 3 and 5. After being formed on the substrates, the alignment layer is rubbed to induce molecules within the layer of liquid crystal material to inherit a predetermined pretilt angle and alignment direction between the first and second substrates 3 and 5 (S102 and S105). Subsequently, spacers are dispensed over the first substrate 3 to maintain a uniform cell gap between the first and second substrates 3 and 5 (S103). The sealant is applied to an outer portion of the first substrate 3 (S106) and the second substrate 5 is pressed and attached to the upper substrate 3 (S107).

The first and second substrates 3 and 5 are formed from glass substrates having an area larger in size than any individual panel areas. Accordingly, a plurality of corresponding panel areas are formed where driving devices and color filter layers are arranged within the attached glass substrates. Thus, in fabricating individual liquid crystal display panels, the attached glass substrates are cut into individual panels (S108). Subsequently, liquid crystal material is injected through a liquid crystal injection opening into the cell gap formed between the two substrates of each individual liquid crystal display panel (S109). After the liquid crystal material is injected, the liquid crystal injection opening is sealed (S109) and each individual liquid crystal display panel is inspected (S110).

As described above, in this fabrication process of the liquid crystal display device, the alignment layers are formed on both the first and second substrates 3 and 5 to provide the align controlling force to the liquid crystal molecules in the liquid crystal layer 7.

FIGS. 3A-3D are views showing the method of forming the alignment layer of this invention.

Figure 3A:
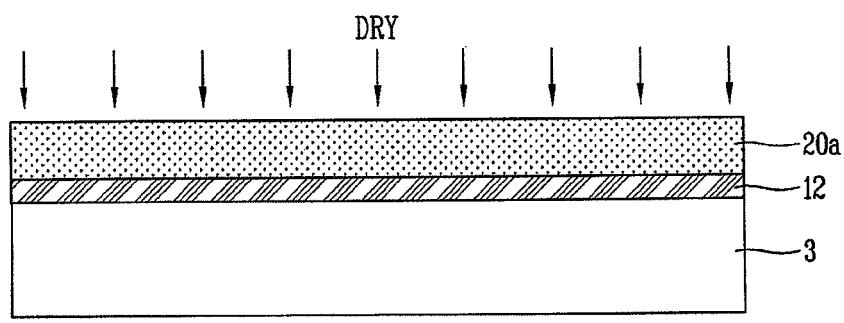
FIGS. 3A-3D are views showing the method of fabricating the alignment layer.

As shown in FIG. 3A, first, the metallic oxide such as ITO (Indium Tin Oixde) or IZO (Indium Zinc Oixde) is deposited on the transparent substrate 3 and then the polyamic acid solution is coated on the metallic oxide to form the polyamic acid layer 20a. At this time, the substrate may be the thin film transistor substrate or the color filter substrate. The polyamic acid solution is formed by reacting the diamine compound and the anhydride in a solvent. Subsequently, the polyamic acid layer 20a on the substrate 3 is heated in the predetermined period to bake softly the polyamic acid layer 20a.

Figure 3B:
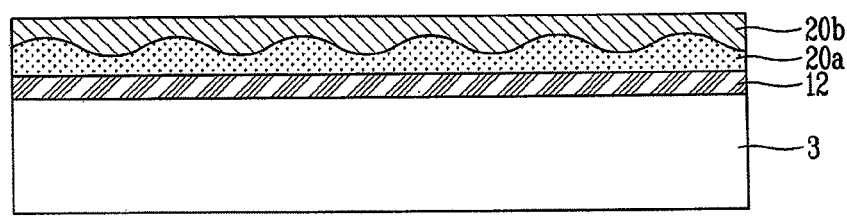

As shown in FIG. 3B, by baking the polyamic acid layer 20a, a part of the polyamic acid layer 20a is converted to the polyimide layer 20b.

Figure 3C:
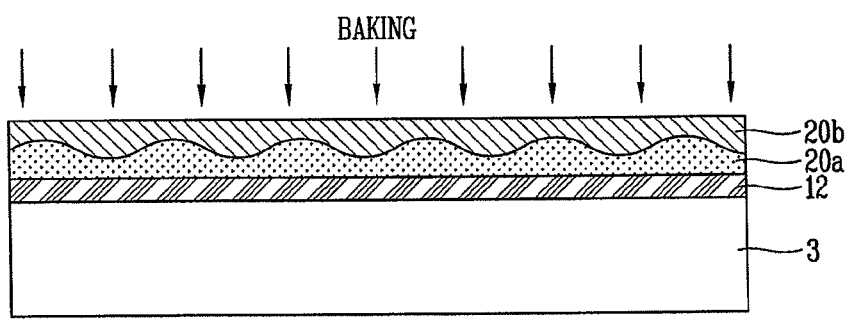

Thereafter, as shown in FIG. 3C, the polyamic acid layer 20a and the polyimide layer 20b undergo a post baking process where they are heated in the predetermined temperature and period.

Figure 3D:
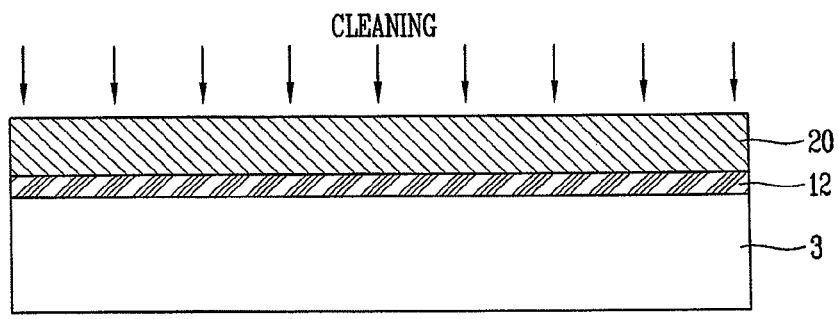

Through the post baking process, as shown in FIG. 3D, the entire polyamic acid layer 20a is totally converted to polyimide so that the alignment layer 20 of the polyimide is formed over the substrate 3. This alignment layer 20 is then cleaned by an isopropane solution.

In this invention, the alignment layer can be formed of a hybrid layer having the polyamic acid layer 20a and the polyimide layer 20b. When the alignment layer 20 is formed of the polyamic acid, the film may be separated from the substrate 3, since the surface area of the polyamic acid is converted to the polyimide. To the contrary, when the alignment layer 20 is formed of the hybrid layer, the film is not separated from the substrate 3.

The hybrid layer can be formed by the same process condition as the polyimide layer and tested by the same test method as the polyimide layer. Thus, the process and test disclosed in this disclosure can be adapted to the polyimide layer and the hybrid layer.

The quality of the alignment layer 20 can be determined by the surface state and the imidization of the alignment layer 20. It is proper to form only the polyimide on the surface of the alignment layer 20. In the liquid crystal display device, when the polyamic acid ions are diffused on the surface of the alignment layer 20, the impurities in the liquid crystal layer are attached to the alignment layer, that is, the polyamic acid ion, since the polyamic acid ion has a polarity. The attachment of the impuries disturbs the arrangement of the liquid crystal molecules in the corresponding region so that the image quality may be deteriorated. Therefore, when the alignment layer is formed, only the polyimide should be formed on the surface of the alignment layer 20 and the diffusion of the polyamic acid ions to the surface of the alignment layer 20 should be prevented by controlling the dry condition of the polyamic acid layer.

The imidization of the alignment layer 20 affect the rubbing characteristic, the alignment controlling degree, and the chemical stability. In other word, the characteristic is determined by the imidization of the alignment layer 20.

In a preferred embodiment of this invention, the method of fabricating the alignment is introduced. Further, the surface of the alignment layer 20 is observed and the imidization of the alignment layer 20 is tested to test the quality of the alignment layer 20. In the related art, there is no separate method for testing the alignment layer 20, so the quality of the alignment layer 20 cannot be tested. In this embodiment, however, it is possible to test separately the alignment layer 20, so that the alignment layer 20 can be tested under various conditions. As a result, it is possible to understand the quality of the alignment layer 20 under the various conditions. In this embodiment, since the process condition of the alignment layer having good quality can be obtained by testing the alignment layer, the fabrication process having good process conditions is provided.

In this embodiment, the surface of the alignment layer 20 is tested by an AFM (Atomic Force Microscope) and the imidization of the alignment layer 20 is tested by FT-IR (Fourier Transformation Infrared Spectroscope). Hereinafter, the test method of the alignment layer 20 using AFM and FT-IR will be described.

Surface Test of the Alignment Layer

The alignment layer can be converted to the polyimide by coating the polyamic acid solution and drying (pre-baking) the coated polyamic acid solution. The conversion to the polyimide is determined by the dry temperature and the dry time of the coated polyamic acid solution. Therefore, in this embodiment, the surface of the alignment layer is tested in accordance with the dry condition to obtain the optimum dry condition.

First, the metallic oxide layer such as ITO is deposited and then the polyamic acid solution is coated on the metallic oxide. Subsequently, the substrates on which the polyamic acid solution is coated are respectively exposed at the atmosphere temperatures of about 120° C., about 145° C., about 165° C., and about 185° C. for about 60 second, about 80 second, and about 100 second to dry the polyamic acid solution. Under the atmosphere temperature of about 120° C., about 145° C., about 165° C., and about 185° C., the substrate is actually dried at the actual temperature of about 53° C., about 60° C, about 65, and about 70° C. By the drying of the polyamic acid solution, the polyimide layer is formed on the metal oxide layer.

Pictures of the alignment layer dried under above conditions is taken using the AFM to observe the surface of the alignment layer. Table 1 shows the state of the surface of the alignment layer.

TABLE 1

|  | 53° C. | 60° C. | 65° C. | 70° C. |
|---|---|---|---|---|
| 60 seconds | X | X | Δ | Δ |
| 80 seconds | X | ○ | ○ | ○ |
| 100 seconds | Δ | ○ | ○ | ○ |

Where, x denotes the surface state that the polyamic acid ions are observed, Δ denotes the surface state that the polyamic acid ions are partially observed, and ○ denotes the surface state that the polyamic acid ions are not observed.

In accordance with the surface test, as shown in Table 1, when the polyamic acid solution coated on the substrate is heated and dried at the actual temperature of approximately about 60-70° C. of the substrate (corresponding to the atmosphere temperature of about 145-185° C.) for about 80-100 seconds, the polyamic acid ions are not diffused to the surface of the alignment layer.

Surface Test of the Cleaned Alignment Layer

In general, the alignment layer is cleaned after coating and baking. The alignment layer is cleaned by the isopropane solution. However, since the cleaning effect of the alignment layer is varied in accordance with the concentration of the isopropane solution and the excessive concentration causes damage to the alignment layer, the isopropane solution should have the proper concentration and cleaning time. In this embodiment, the optimum cleaning conditions is obtained by testing the surface of the alignment layer according to the various cleaning conditions.

First, the alignment layer on the substrate is baked and the baked alignment layer is dipped in the cleaning tank having the isopropane solution to clean the baked alignment layer. At this time, the alignment layer is dipped in the isopropane solution having the concentration of about 20%, about 30%, about 40%, about 60%, and about 60% for about 10 second, about 30 second, about 60 second, about 90 second, and about 180 second, respectively.

Thereafter, the cleaned alignment layer is dried and a picture is taken by the AFM to observe the cleaning of the alignment layer. Table 2 shows the observation result of the alignment layer to be cleaned in accordance with above cleaning conditions.

TABLE 2

|  | 0% isopropane solution | 20% | 30% | 40% | 60% |
|---|---|---|---|---|---|
| 10 seconds | X | Δ | Δ | X | X |
| 30 seconds | Δ | ○ | ○ | Δ | X |
| 60 seconds | Δ | ○ | ○ | Δ | X |
| 90 seconds | Δ | ○ | ○ | Δ | X |
| 180 seconds | X | X | X | X | X |

Where, x denotes the state where the surface of the alignment layer is not cleaned and the alignment layer is damaged, Δ denotes the state that the surface of the alignment layer is partially cleaned and the alignment layer is partially damaged, and ○ denotes the state that the alignment layer is totally cleaned.

As shown in Table 2, in the cleaning test of this embodiment, the alignment layer is totally cleaned and the damage of the alignment is prevented, when the alignment layer is dipped in the isopropane solution of about 20-30% concentration for about 30-90 seconds. When the alignment layer is cleaned in the isopropane solution of less than about 10%, the alignment layer is not cleaned. Further, when the the alignment layer is cleaned in the isopropane solution of more than about 40%, the isopropane is attached on the alignment layer so that the alignment layer may be damaged.

Test of Imidization of the Alignment Layer

The imidization of the alignment is a very important factor for the rubbing characteristics, the alignment controlling degree, and the chemical stability. The imidization of the alignment layer is achieved by baking the alignment layer. The alignment layer should be totally imizidized for the alignment layer to have good quality. In this case, however, since the alignment layer is baked for too long, the process may be delayed. Therefore, in this embodiment, the property of the alignment layer is tested in accordance with the baking condition to obtain the optimum condition in which the alignment layer can be rapidly imidized.

First, the polyamic acid solution of approximately 0.5 mm is coated on the substrate and baked at the temperature of about 230° C. and about 240° C. for about 300-2000 seconds. Thereafter, the property of the baked alignment layer is detected using the FT-IR. At this time, a crystalline substrate such as NaCl is used for the substrate, since NaCl has a simple molecule structure so that the effect caused by the IR can be minimized when the IR is irradiated to the substrate.

Figures 4, 5:
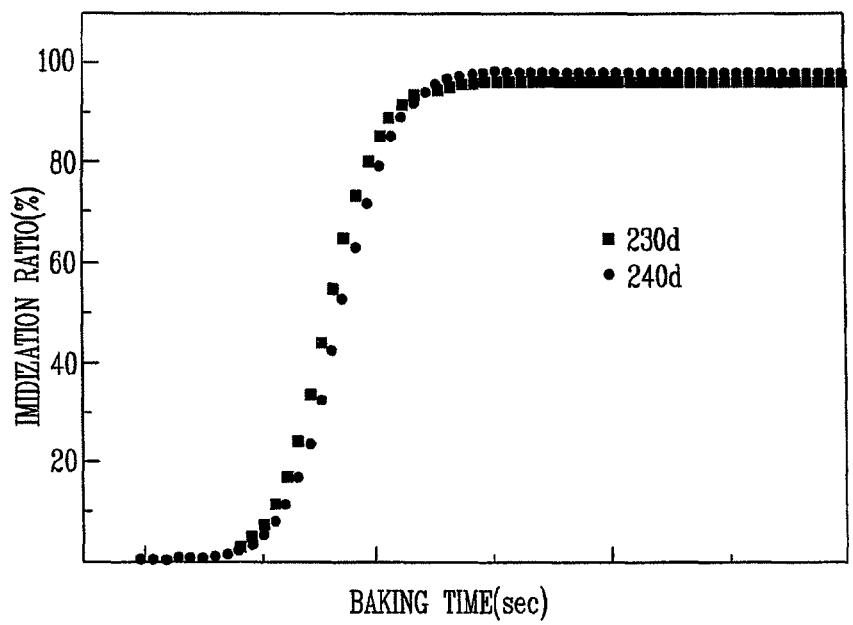
FIG. 4 is a graph showing the relationship between the soft time and the imidization of the alignment layer.
FIG. 5 is a flow chart showing the method of fabricating the alignment layer.

FIG. 4 is a graph showing the relationship between the soft time and the imidization of the alignment layer. As shown in FIG. 4, when the polyamic acid solution is baked at the temperature of about 230° C. and about 240° C., the imidization of the alignment layer is rapidly increased in the soft time of more than approximate about 500 seconds so that approximately about 90% of the alignment layer is imidized in the soft time of approximate about 1000 seconds.

If the soft time is increased, the imidization of the alignment layer is also increased, but at the same time imidization ratio is trivially increased. When more than about 90% of the alignment layer is imidized, the rubbing characteristic, the alignment controlling degree, and the chemical stability is good and thus the inferiority is not occupied in the alignment layer. That is, when the alignment layer is baked at the temperature of about 230° C. and about 240° C. for more than about 1000 seconds, the alignment layer is greatly imidized.

As described above, in this embodiment, the surface state, the cleaning state, and the imidization of the alignment layer are tested, so that the inferiority of the alignment layer can be rapidly determined. Further, since the alignment layer can be formed in accordance with the fabrication conditions of the alignment layer which is obtained in each test process, the quality of the alignment layer can be increased.

Hereinafter, we will describe the method of fabricating the alignment layer using the conditions obtained in the test of the alignment layer as follows.

FIG. 5 is a flow chart showing the fabrication method of the alignment layer. This method is identical to that shown in FIG. 3a-3d, but this method includes the detailed conditions of the process. Thus, the alignment layer according to this embodiment may be formed by the process shown in FIG. 3a-3d and the process conditions shown in FIG. 5.

As shown in FIG. 5, the polyamic acid solution is coated on the substrate on which the metallic oxide such as ITO and IZO is deposited to form the polyamic acid layer (S201). Subsequently, the polyamic acid layer is dried at the actual temperature of about 60-70° C. (corresponding to the atmosphere temperature of about 145-185° C.) for about 80-100 seconds (S202). By this drying process, the polyamic acid layer begins to convert to the polyimide layer.

Thereafter, the dried polyamic acid layer is heated at the temperature of approximate about 230° C. or about 235° C. for approximately about 1000 seconds to bake the polyamic acid layer (S203). By this baking, more than about 90% of the polyamic acid layer is imidized so that the polyimide layer is formed on the substrate. Subsequently, the baked alignment layer is dipped in the isopropane solution having the concentration of about 20-30% for approximately more than about 1000 seconds to clean the alignment layer (S204).

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

The invention claimed is:

1. A method of fabricating an alignment layer, comprising:
coating an alignment material comprising a polyamic acid on a substrate;
drying the alignment material at an actual temperature of about 60-70° C. for about 80-100 seconds;
scanning the surface of the dried alignment material with an Atomic Force Microscope to confirm that no polyamic acid ions are on the surface of the dried alignment material immediately after the drying of the alignment material;
baking the dried alignment material at a temperature of about 230° C. or about 235° C. for more than about 1000 seconds to form the alignment layer after the scanning of the surface of the dried alignment material; and
cleaning the baked alignment layer.

2. The method of claim 1, wherein the cleaning the baked alignment layer includes dipping the baked alignment layer in an isopropane solution for more than about 1000 seconds.

3. The method of claim 1, wherein the polyamic acid is converted to a polyimide by drying and baking the polyamic acid.

4. The method of claim 1, wherein the actual temperature of about 60-70° C. corresponds to an atmosphere temperature of about 145-185° C.

5. The method of claim 1, wherein about 90% of the alignment material is imidized during the baking of the dried alignment material.

* * * * *